United States Patent [19]

Mise et al.

[11] Patent Number: 4,837,020
[45] Date of Patent: Jun. 6, 1989

[54] DEODORANT COMPOSITION

[75] Inventors: Noritoshi Mise, Takatsuki; Koichi Matsumura, Ibaraki, both of Japan

[73] Assignee: Takeda Chemical Industries, Ltd., Osaka, Japan

[21] Appl. No.: 94,609

[22] Filed: Sep. 9, 1987

[30] Foreign Application Priority Data

Sep. 9, 1986 [JP] Japan .................... 61-212954

[51] Int. Cl.$^4$ ............................ A61K 7/38
[52] U.S. Cl. ........................... 424/68; 424/65
[58] Field of Search ...................... 424/65, 68

[56] References Cited

U.S. PATENT DOCUMENTS 3,954,989 5/1976 Mecca .................... 424/68 X
4,172,123 10/1979 Lowicki .................. 424/65 X

FOREIGN PATENT DOCUMENTS 130307 3/1978 Fed. Rep. of Germany ...... 424/65
60-136506 7/1985 Japan ........................ 424/65

OTHER PUBLICATIONS

Derwent Publications LTD. Abstract of Japanese Patent J5 9132-937-A "Agent for Removal of Ammonia and Mercaptan Odour-Comprises L-Ascorbic Acid and Ferrous Cpd. Supported on Substance Contg. Active Carbon or Contained in Paper or Cloth."

Derwent Publications Ltd. Abstract of Japanese Patent J60142 856 A "Powdery Composition Containing Ferrous Compound-Useful as Deodorant for Cosmetic, Pharmaceutical, Flame Retardant, etc."

*Primary Examiner*—W. J. Shine
*Attorney, Agent, or Firm*—Wenderoth, Lind & Ponack

[57] ABSTRACT

A deodorant composition comprising (a) D-glucosaccharoascorbic acid and (b) a ferrous compound and/or a cupric compound is disclosed. The composition displays excellent deodorant effects by removing the offensive and foreign odors rapidly, irrespective of whether they are originating from basic substances such as ammonia or those from acid substances such as hydrogen sulfide.

7 Claims, No Drawings

DEODORANT COMPOSITION

The offensive and foreign odors which are considered objectionable in the living environment generally originate from various installations such as a raw sewage disposal plant, animal pen, fish meat packing plant, etc. or from the water closet, dust bin, refrigerator, and so on. Generally these malodors are mostly caused by the putrefaction and decomposition of organic constituents of animals and plants, and are attributed to basic substances such as ammonia and amines and acid substances such as hydrogen sulfide, mercaptans and so on. For the elimination of such malodors, a variety of methods have been proposed. Such methods include the method for adsorptive removal of odoriferous substances with a porous material such as activated carbon, silica gel, zeolite, etc., as used either as it is or after chemical treatment, and the method comprising an acid decomposition of malodorous substances with a chemical agent such as hypochlorous acid and the method of neutralizing them with a chemical agent such as an acid or an alkali. On the other hand, various deodorant compositions for practicing these methods have been developed and put to use.

Recently, compositions comprising L-ascorbic acid in combination with a compound of divalent iron such as ferrous sulfate have been reported and gathering attention as having a very effective deodorant action (For example, Japanese Patent Application Laid-Open No. 132937/1984 and No. 142856/1985;Derwent Publications Ltd. Abstract Nos. 84-223002/36 and 85-220755/36). It is true that such deodorant compositions are excellent in deodorant effects but their use is seriously delimited by the fact that a variation in the proportions of the two ingredients results in a drastic change in effect. For example, while the absorption of ammonia is maximal at the very low level of L-ascorbic acid, the composition is then apt to undergo degradation, thus presenting a stability problem.

One of the present inventors who was undertaking a research for the synthesis of L-ascorbic acid, D-erythorbic acid and their related compounds found that treating 2-keto-D-glucaric acid or its 2,3-O-acetal with an acid yields D-glucosaccharoascorbic acid, a novel compound (European Patent Application Publication No. 0228273, Pub. date 1987. 7. 8.) Paying attention to the structural feature that unlike L-ascorbic acid or D-erythorbic acid, this new compound has a carboxyl group within its molecule, the present inventors sought for the development of new uses for the compound and found that a composition obtainable by adding a ferrous compound or a cupric compound to D-glucosaccharoascorbic acid has an excellent deodorant action. It was also found that this composition exhibits stable effects in a broader range of the ratio of the two ingredients. The present invention has been accomplished on the basis of the above findings.

Thus, the present invention relates to a deodorant composition comprising (a) D-glucosaccharoascorbic acid and (b) a ferrous compound and/or a cupric compound.

The compound (a) to be used in this invention is a novel compound, the chemical name of which is D-erythro-hexo-2-enaro-1,4-lactone and which has not been described in the literature. This compound can be produced by treating 2-keto-D-glucaric acid or a salt thereof or 2,3-O-acetal or ketal thereof with an acid (for example, hydrogen chloride, sulfuric acid, etc.) in water or an organic solvent. The starting material 2-keto-D-glucaric acid can for example be prepared by subjecting D-glucose to one-stage fermentive oxidation reaction using a strain of the genus *Pseudogluconobacter* [for example, *Pseudogluconobacter saccharoketogenes* K 591s (Deposited at Fermentation Research Institute (FRI) as FERM P-8481 on Oct. 7, 1987 and at Institute for Fermentation, Osaka as IFO 14464 on Sept. 19, 1985. Also deposited at FRI as BP-1130)].

In the practice of the present invention, D-glucosaccharoascorbic acid may be used either in the free acid form or in the form of an alkali metal salt (for example, sodium salt, potassium salt) or an alkaline earth metal salt (for example, calcium salt).

As the second ingredient (b) of the composition of the invention, a water-soluble ferrous compound or a water-soluble cupric compound can be used. As examples of such compounds, ferrous (II) salts of inorganic acids such as sulfuric acid, hydrochloric acid, nitric acid, etc. and cupric (II) salts of similar inorganic acids can be mentioned. Specific examples include such ferrous compounds as ferrous sulfate, ferrous chloride, ferrous nitrate etc. and such cupric compounds as cupric sulfate, cupric chloride, cupric nitrate and so on. Such oxides as cupric oxide may also be employed.

The ratio of (a) to (b) is 0.001 to 2 moles of (a) to each mole of (b), preferably 0.01 to 1 mole of (a) on the same basis, and still more desirably 0.1 to 1 mole (a) on the same basis.

The deodorant composition according to the present invention may be either a liquid or a solid, only if it contains (a) and (b). To use the composition in liquid form, an aqueous solution or dispersion of (a) and (b) is prepared. The concentration of the deodorant composition is not particularly critical and may be selected in consideration of the solubility or dispersibility of (a) and (b) in water.

For use as a solid composition, the two components (a) and (b) may be mixed, both in powdery state, evenly to give the desired composition. Preferably, however, the two components are previously dissolved in water or a hydrophilic solvent (a lower alcohol such as methanol, ethanol, etc. or a ketone such as acetone, etc.) and the water or solvent is removed by the conventional drying technique (such as vacuum drying, spray drying, lyophilization, etc.). The resulting solid deodorant composition may be used as it is or as prepackaged in a container. Preferred forms of use are as follows.

(A) Support on a porous material such as activated carbon, activated alumina, zeolite, vermiculite, sepiolite and so on. Deposition on such a porous material can be accomplished by preparing a solution of the deodorant composition, impregnating the porous material with the solution and drying the same. A deodorant product having excellent deodorizing activity can be manufactured by selecting an alkaline porous material such as activated alumina, which is among said porous materials, and depositing the deodorant composition thereon.

(B) Support of the deodorant composition on any of various substrates such as paper, cloth, nonwoven fabric, plastic film, etc. by impregnation or coating, followed by drying.

(C) Compounding of the deodorant composition with a plastic material or synthetic resin and subsequent molding.

The deodorant composition according to this invention can be used as it is or in any desired form such as those mentioned by allowing it to stand in a place where an offensive or foreign odor is evolved or by spraying it directly to sources of such malodors. The amount of application can be selected as required in consideration of the amount of malodor, the type and source of the malodor, and other conditions.

The deodorant composition according to this invention displays excellent deodorant effects by removing the offensive and foreign odors rapidly, irrespective of whether they are originating from basic substances such as ammonia or those from acid substances such as hydrogen sulfide. Furthermore, the composition is very stable with little degradation such as rusting so that it is of great practical value.

The following working and reference examples are further illustrative of the invention.

WORKING EXAMPLES

Example 1

In 150 ml of methanol was dissolved 13.9 g of ferrous sulfate heptahydrate, while 2.3 g of D-glucosaccharoascorbic acid was dissolved in 50 ml of methanol. The two solutions were combined and concentrated under reduced pressure at about 40° C. in a rotary evaporator to give a crystalline deodorant composition. A glass tube with an inner diameter of 6 mm was filled with 0.5 g of the above deodorant composition and stoppered with glass wool at both ends to give a sample tube. This sample tube was passed through a circulating air including foreign-odor substances (ammonia and methylmercaptan) in a closed 20-liter vessel for exposure of the deodorant composition. The initial concentrations of the foreign-odor substances and the concentrations after predetermined time periods were determined. These determinations were carried out with Gastek® (for ammonia and mercaptans) from Kitazawa Sangyo Co., Ltd. The results are set forth in the following table.

| Time (in minutes) | Ammonia | Methylmercaptan |
|---|---|---|
| 0 (initial value) | 70 ppm | 32 ppm |
| 10 | 23 | 27 |
| 30 | 7 | 22 |
| 60 | 2 | 19 |

Example 2

In 30 ml of distilled water was dissolved 13.9 g of ferrous sulfate heptahydrate followed by addition of 2.3 g of D-glucosaccharoascorbic acid. The mixture was stirred to dissolve the acid and, then, made up with distilled water to make 50 ml. This solution was used as a stock solution. To 10 ml of this stock solution was added 10 ml of distilled water for dilution and 20 g of activated alumina (Neobeads® MSDL-3, Mizusawa Chemical Co., Ltd.) was immersed therein with sufficient stirring. This composition was dried under reduced pressure in a silica gel desiccator to give an activated alumina-supported deodorant composition (Sample A). This sample A was packed into a glass tube (in. dia. 15.6 mm, length 50 mm) (packing volume 10 ml). Then, a mixed carrier gas of air and nitrogen (8:2, v/v; 80% RH) containing 30±2 ppm of $NH_3$, 15±3 ppm of $H_2S$ and 3±1 ppm of $CH_3SH$ was introduce into the above deodorant tube. The initial concentrations (Co) of the foreign-odor substances and the concentrations (Ct) after passage through the sample were determined and the ratio Ct/Co was calculated and shown in percentage. This gas permeability rate was determined at predetermined time intervals. The gas was introduced at a flow rate of 4.6 l/min and controlled to an intratube flow rate of 40 cm/sec. This experiment was performed with both the sample and the gas being preadjusted to about 25° C. The concentrations of foreign-odor substances were determined using a detection tube (3L for ammonia, Kitazawa Sangyo Co., Ltd.) for $NH_3$ and by gas chromatography for $H_2S$ and $CH_3SH$. The results are shown in Table 1.

Example 3

An activated alumina-supported deodorant composition was manufactured in accordance with the same procedure and conditions as Example 2 except that 13.9 g of ferrous sulfate heptahydrate and 1.14 g of D-glucosaccharoascorbic acid were used (sample B) and the gas absorbing capacity of the product was determined. The results are set forth in Table 1.

Example 4

A deodorant composition supported on activated alumina (Sample C) was manufactured in accordance with the same procedure and conditions as set forth in Example 2 except that ferrous sulfate heptahydrate and D-glucosaccharoascorbic acid were used in the amounts of 27.8 g and 4.6 g, respectively, and the absorptive capacity of the sample was determined. The results are shown in Table 1.

A further deodorant composition (Sample D) was manufactured in accordance with the same procedure and conditions as set forth in Example 2 except that only ferrous sulfate heptahydrate was used in the amount of 13.9 g and the gas absorbing capacity was determined. The gas absorbing capacity of activated alumina alone (Sample E) was also determined. The results are set forth in Table 1.

TABLE I

| | | Gas permeability rates (%) of deodorant compositions (Samples A through E) | | | | | |
|---|---|---|---|---|---|---|---|
| | | | | Time | | | |
| Sample | Malodorous substances | Initial | 2 | 4 (hrs) | 8 | 16 | 32 |
| A | Ammonia | 0 | 0 | 0 | 15 | 80 | 96 |
| | Hydrogen sulfide | 76 | 76 | 76 | 75 | 72 | 70 |
| | Methylmercaptan | 91 | 91 | 90 | 90 | 85 | 82 |
| B | Ammonia | 0 | 0 | 0 | 31 | 85 | 100 |
| | Hydrogen sulfide | 100 | 75 | 87 | 82 | 75 | 73 |
| | Methylmercaptan | 100 | 95 | 90 | 84 | 72 | 63 |
| C | Ammonia | 0 | 0 | 0 | 0 | 25 | 80 |
| | Hydrogen sulfide | 92 | 88 | 83 | 79 | 79 | 78 |
| | Methylmercaptan | 100 | 90 | 84 | 80 | 80 | 80 |
| D | Ammonia | 0 | 0 | 60 | 80 | 90 | 100 |
| | Hydrogen sulfide | 100 | 90 | 96 | 90 | 90 | 88 |
| | Methylmercaptan | 100 | 95 | 97 | 95 | 90 | 90 |
| E | Ammonia | 20 | 70 | 90 | 97 | 98 | 98 |
| | Hydrogen sulfide | 95 | 95 | 95 | 95 | 96 | 98 |
| | Methylmercaptan | 100 | 97 | 100 | 100 | 100 | 100 |

Example 5

In 35 ml of distilled water was dissolved 12.50 g of cupric sulfate pentahydrate followed by addition and dissolution of 5.7 g of D-glucosaccharoascorbic acid. The solution was then diluted with distilled water to make 50 ml for use as a stock solution. To 10 ml of this stock solution was added 10 ml of distilled water for dilution and 20 g of activated alumina (Neobeads® MSDL-3) was immersed therein with sufficient stirring.

The composition was taken out and dried under reduced pressure in a silica gel desiccator to give an activated alumina-supported deodorant composition (Sample F). A deodorant composition (Sample G) was also manufactured in the same manner as above except that D-glucosaccharoascorbic acid was used in an amount of 2.3 g instead of 5.7 g. A deodorant composition (Sample H) was also manufactured in the same manner by supporting 12.5 g of cupric sulfate pentahydrate alone on activated alumina. The gas absorbing capacities of these samples F through H were determined in the same manner as Example 2. The results are set forth in Table II.

TABLE II

Gas permeability rates (%) of deodorant compositions (Samples F through H)

| Sample | Malodorous substances | Initial | 2 | 4 | 8 | 16 | 32 |
|---|---|---|---|---|---|---|---|
| | | | | (hrs) | | | |
| F | Ammonia | 0 | 0 | 0 | 18 | 60 | 78 |
| | Hydrogen sulfide | 0 | 0 | 30 | 46 | 47 | 46 |
| | Methylmercaptan | 0 | 0 | 20 | 39 | 41 | 45 |
| G | Ammonia | 0 | 0 | 0 | 20 | 70 | 95 |
| | Hydrogen sulfide | 0 | 0 | 9 | 10 | 10 | 3 |
| | Methylmercaptan | 0 | 0 | 5 | 7 | 4 | 2 |
| H | Ammonia | 0 | 0 | 15 | 48 | 78 | 90 |
| | Hydrogen sulfide | 0 | 10 | 30 | 49 | 60 | 70 |
| | Methylmercaptan | 0 | 0 | 12 | 35 | 57 | 64 |

Example 6

The trimethylamine absorbing capacities of the deodorant composition (Sample A) manufactured in Example 2 and the deodorant composition (Sample G) manufactured in Example 5 were determined. Thus, a 20-liter glass bottle was charged with 1.5 ml of an ethanolic solution containing 1 μg of trimethylamine in each μl of ethanol and the trimethylamine was evaporated with adjustment of the volume of ambient air to prepare a mixed air containing 50–60 ppm of trimethylamine vapor.

On the other hand, a glass tube (in. dia. 6 mm, length 40 mm) was packed with 1 g of Sample A and the above mixed gas was introduced into the tube at a flow rate of 3.0 l/min. At predetermined time intervals, the concentration of trimethylamine in the circulating mixed gas was determined with a Gastek ® detection tube (Kitazawa Sangyo Co., Ltd., No. 180 for amines). The same experiment was performed with Sample G. The results are set forth in Table III.

TABLE III

| Sample | Time Before circulation | At 10 min. of circulation | At 60 min. of circulation |
|---|---|---|---|
| A | 60 ppm | 25 ppm | 2 ppm |
| B | 50 | 24 | 4 |

Example 7

In 80 ml of water were dissolved 2.5 g of ferrous sulfate heptahydrate and 0.5 g of D-glucosaccharoascorbic acid followed by addition of 60 g of activated alumina (Mizusawa Chemical, Neobeads ® MSDL-3). After allowing to stand for a while, the mixture was concentrated under reduced pressure. When the liquid had evaporated off, the concentrate was put in a silica gel desiccator for dehydration under reduced pressure to give a deodorant composition. One gram of this deodorant composition was packed into a Pyrex tube, which was then stoppered with glass wool at both ends to give a sample tube. This tube was supplied with a malodorous gas (in a 20-litter gas holder) preadjusted to a predetermined concentration by means of a pump for exposure of the deodorant to the malodorous gas. The mixed gas was sampled at predetermined intervals for determination of the concentration of malodorous gas and the time course of its concentration was monitored. The flow rate of the gas was 3 l/min. The concentrations of malodorous gases were determined by gas chromatography for sulfur compounds and using a detection tube for ammonia. The results are set forth in Table IV.

TABLE IV

| Malodorous gas Time (in min.) | Hydrogen sulfide | Methyl-mercaptan | Ammonia |
|---|---|---|---|
| 0 | 26 ppm | 44 ppm | 42 ppm |
| 5 | 23.2 | 33 | 26 |
| 15 | 21.8 | 30 | 14 |
| 25 | 20.1 | 24 | 8 |
| 35 | 18.8 | 21 | 5 |
| 45 | 17.7 | 18 | 3 |
| 105 | 13.1 | — | 0 |

Note — denotes no determination.

Example 8

In 40 ml of water were dissolved 10 g of ferrous chloride and 2.3 g of D-glucosaccharoascorbic acid followed by addition of distilled water to make 50 ml. To 10 ml of this solution was added 10 ml of distilled water for dilution and 20 g of activated alumina was immersed in this dilution, followed by drying to give an activated alumina-supported deodorant composition. A glass tube with an inside diameter of 6 mm was packed with 1 g of the above deodorant composition to give a sample tube. Then, ammonia-containing air was circulated through this test tube for continuous contact and the concentration of ammonia was determined at predetermined time intervals. The results are shown below in the table. A blank test was performed with activated alumina alone.

| Time (in min.) | Deodorant of Example 8 | Activated alumina (blank) |
|---|---|---|
| 0 (initial value) | 54 ppm | 50 ppm |
| 20 | 10 | 24 |
| 60 | 3 | 13 |
| 70 | 0 | 11 |

Example 9

In 20 ml of distilled water were put 1.6 g of cupric oxide and 0.4 g of D-glucosaccharoascorbic acid. Then, with stirring, 20 g of activated alumina (Mizusawa Chemical, Neobeads ® MSDL-3) was added. After thorough mixing so as to saturate the alumina evenly with the solution, the alumina was dried in a silica gel desiccator under reduced pressure to give an activated alumina-supported deodorant composition. A glass tube with an inner diameter of 6 mm was packed with 1 g of this deodorant composition and an air containing malodorous substances (ammonia and methylmercaptan) was circulated through the tube in a glass vessel for continuous contact with the deodorant. The concentrations of malodorous gases were determined at predetermined intervals and the gas absorbing capacities of the deodorant were determined. The results are set forth below in the table. All determinations were made using a gas detection tube (Gastek®, Kitazawa Sangyo Co., Ltd.).

| Time (in min.) | Malodorous components Ammonia | Methylmercaptan |
|---|---|---|
| 0 (initial value) | 70 ppm | 35 ppm |
| 15 | 16 | 30 |
| 30 | 1 | 23 |
| 60 | 0 | 20 |

Example 10

A craft paper-supported deodorant composition was manufactured as follows:

1 l of 12.9 wt % aqueous solution of D-glucosaccharoascorbiic acid, 1 l of 18.3 wt % aqueous solution of cupric sulfate pentahydrate and 0.5 l of 10 wt % aqueous solution of polyvinylalcohol were mixed. The craft paper (940 mm×640 mm×0.5 mm) was roll-coated with this mixture and dried. After one week the deodorizing activity of this deodorant paper was measured at 25° C. by setting a sample (15 cm×15 cm) in a 11.4 l desicator which was filled with air containing ammonia gas. The concentration of ammonia in the desicator after 24 hours was compared with initial one. The results are set forth in the following table.

| Amount of deodorant*[1] on the craft paper (as $CuSO_4$, mg/ (15 cm × 15 cm)) | Initial concentration ppm*[2] | After 24 hours ppm |
|---|---|---|
| 76.7 | 1350 | 400 |
| 0 | 1300 | 600 |

The calculated amount of absorbed ammonia by deodorant composition is 96.4 mg/m².
*[1]Measured by ion chromatographic analysis of the extract in water of the coated craft paper.
*[2]Observed using a detection tube (3L-for ammonia, Kitagawa Sangyo Co., Ltd.)

Example 11

A polypropylene nonwoven cloth-supported deodorant composition was prepared and the deodorant activity to ammonia was measured in accordance with the same procedure and condition as in Example 10. The results are shown below.

| Amount of deodorant on the nonwoven cloth* (as $CuSO_4$, mg/ (15 cm × 15 cm)) | Initial concentration ppm | After 6 hours concentration ppm |
|---|---|---|
| 45.2 | 1300 | 700 |
| 0 | 1300 | 900 |

The calculated amount of absorbed ammonia by deodorant composition is 77.3 mg/m².
*The grade of PP nonwoven cloth used was 17 g/m².

Example 12

An activated alumina-supported deodorant composition was manufactured in accordance with the same procedure and conditions as in Example 2 except that 13.9 g of ferrous sulfate heptahydrate and 2.9 g of D-glucosaccharoascorbic acid disodium salt were used and the gas absorbing capacity of the product was determined. The results are set forth in the following table.

| Malodorous substances | Initial | 2 | 4 | 8 (hours) | 16 | 32 |
|---|---|---|---|---|---|---|
| Ammonia | 0 | 0 | 0 | 20 | 100 | 100 |
| Hydrogen sulfide | 90 | 83 | 80 | 79 | 81 | 81 |
| Methyl mercaptan | 100 | 95 | 90 | 91 | 83 | 85 |

Example 13

An activated alumina-supported deodorant composition was prepared in accordance with the same procedure and conditions as in Example 2 except that 12.5 g of cupric sulfate pentahydrate and 2.9 g of D-glucosaccharoascorbic acid calcium salt were used and the gas absorbing capacity of the product was determined. The results are set forth in the following table.

| Malodorous substances | Time Initial | 2 | 4 | 8 (hours) | 16 | 32 |
|---|---|---|---|---|---|---|
| Ammonia | 0 | 0 | 0 | 48 | 71 | 80 |
| Hydrogen sulfide | 0 | 0 | 40 | 49 | 52 | 52 |
| Methyl mercaptan | 0 | 0 | 23 | 41 | 41 | 50 |

Reference Example 1

A 200 ml conical flask was charged with 20 ml of a seed culture medium composed of 2.0% of D-glucose, 1.0% of peptone, 1.0% of dried yeast and 2.0% of $CaCO_3$ and sterilized by autoclaving at 120° C. for 20 minutes. This flask was inoculated with a loopful of *Pseudogluconobacter saccharoketogenes* K591s (FERM BP-1130:FERM P-8481: IFO 14464) which had been grown on a slant medium composed of 2.5% of D-sorbitol, 1.0% of peptone, 1.0% of yeast extract, 0.2% of $CaCO_3$ and 2.0% of agar at 28° C. for 4 days. The inoculated flask was incubated under shaking (200 rpm) at 30° C. for 2 days to give a seed culture. Then, a 1-liter conical flask containing 200 ml of the same medium as used for seed culture was inoculated with 10 ml of the above seed culture and incubated under shaking at 30° C. for 3 days.

The resulting broth contained 19.4 mg/ml of 2-keto-D-glucaric acid.

A 1600 ml portion of this culture was centrifuged (7,000 rpm, 10 min.) to remove the cells and other solids, whereby 1520 ml of a supernatant was obtained. This supernatant was cooled to 4° C. and allowed to stand for 3 days. This procedure gave atypical crystals of dicalcium 2-keto-D-glucarate. The crystals were collected on a glass filter (No. 3), washed with small amounts of cold water, methanol and ethyl ether, and dried over phosphorus pentoxide under reduced pressure to give 18 g of dicalcium 2-keto-D-glucarate trihydrate. The physicochemical properties of the resulting crystals were as follows.

Melting point: 152°–157° C. (decompn.)

Elemental analysis (%): $C_6H_6O_8 \cdot Ca \cdot 3H_2O$: Calcd.: C; 24.00, H; 4.03, Ca; 13.35. Found: C; 23.96, H; 4.16, Ca; 13.00.

| | |
|---|---|
| Specific rotation $[\alpha]_D^{25}$ | = −12.3° (c = 1.065%, 0.1N—HCl, immediately after dissolution) |
| | = +7.9° (c = 1.065%, 0.1N—HCl, |

| -continued |
|---|
| after stabilization) |

Reference Example 2

In 800 ml of acetone was suspended 50.0 g of crude dicalcium 2-keto-D-glucarate [containing 85.1% of dicalcium 2-keto-D-glucarate trihydrate ($C_6H_6O_8Ca.3H_2O$) as assayed by high performance liquid chromatography; 0.1417 mole] and under stirring at room temperature, 7.19 g of 97% sulfuric acid (0.17 mole) was gradually added dropwise. After completion of the dropwise addition, the suspension was further stirred for 10 hours. The insolubles were filtered off and washed with about 300 ml of acetone. The washings were combined with the filtrate and concentrated to dryness under reduced pressure. To the residue was added 100 ml of concentrated hydrochloric acid and the mixture was heated at 70° C. for 20 minutes. The reaction mixture was concentrated to dryness under reduced pressure. To the residue were added 100 ml of water and 0.5 g of activated carbon and the mixture was heated at 70° C. for 5 minutes. The mixture was filtered to remove the carbon and the filtrate was concentrated to dryness under reduced pressure. To the residue were added ether and acetonitrile and the insolubles were collected by filtration, washed with a small amount of dichloromethane, and dried under reduced pressure in a desiccator to give 22.2 g of D-gucosaccharoascorbic acid monohydrate (Purity 98.8%). Yield 74.4%. Melting point: 188°-189° C. (decompn.; recrystallized from acetone-benzene).

We claim:

1. A deodorant composition comprising (a) D-glucosaccharoascorbic acid and (b) a ferrous compound and/or a cupric compound.

2. A deodorant composition according to claim 1, wherein the ratio of (a) to (b) is 0.001 to 2 moles of (a) to each mole of (b).

3. A deodorant composition according to claim 1, wherein the ferrous compound is a water-soluble ferrous compound.

4. A deodorant composition according to claim 3, wherein the water-soluble ferrous compound is a ferrous salt of an inorganic acid.

5. A deodorant composition according to claim 1, wherein the components (a) and (b) are deposited on a porous material.

6. A deodorant composition according to claim 5, wherein the porous material is an alkaline porous material.

7. A deodorant composition according to claim 6, wherein the alkaline porous material is activated alumina.

* * * * *